(12) United States Patent
Hill et al.

(10) Patent No.: US 9,168,272 B2
(45) Date of Patent: Oct. 27, 2015

(54) BIOACTIVE GLASS COMPOSITION

(75) Inventors: Robert Hill, London (GB); Delia Brauer, Jena (DE); David G. Gillam, London (GB); Natalia Karpukhina, London (GB); Andrew Bushby, London (GB); Mohammad Mneimne, London (GB)

(73) Assignee: Queen Mary and Westfield College, London (GB)

( * ) Notice: Subject to any disclaimer, the term of this patent is extended or adjusted under 35 U.S.C. 154(b) by 27 days.

(21) Appl. No.: 13/805,852

(22) PCT Filed: Jun. 24, 2011

(86) PCT No.: PCT/GB2011/000958
§ 371 (c)(1),
(2), (4) Date: Mar. 14, 2013

(87) PCT Pub. No.: WO2011/161422
PCT Pub. Date: Dec. 29, 2011

(65) Prior Publication Data
US 2013/0171220 A1   Jul. 4, 2013

(30) Foreign Application Priority Data
Jun. 25, 2010   (GB) .................................. 1010758.9

(51) Int. Cl.
| | |
|---|---|
| *A61K 33/42* | (2006.01) |
| *A61K 8/25* | (2006.01) |
| *A61K 33/16* | (2006.01) |
| *A61K 8/21* | (2006.01) |
| *A61L 27/10* | (2006.01) |
| *A61L 27/12* | (2006.01) |
| *A61K 8/27* | (2006.01) |
| *C03C 3/062* | (2006.01) |
| *C03C 4/00* | (2006.01) |
| *C03C 10/16* | (2006.01) |
| *A61K 8/19* | (2006.01) |
| *A61K 8/24* | (2006.01) |
| *A61K 33/00* | (2006.01) |
| *A61K 33/08* | (2006.01) |
| *A61K 33/30* | (2006.01) |

(52) U.S. Cl.
CPC . *A61K 33/42* (2013.01); *A61K 8/19* (2013.01); *A61K 8/21* (2013.01); *A61K 8/24* (2013.01); *A61K 8/25* (2013.01); *A61K 8/27* (2013.01); *A61K 33/00* (2013.01); *A61K 33/08* (2013.01); *A61K 33/16* (2013.01); *A61K 33/30* (2013.01); *C03C 3/062* (2013.01); *C03C 4/0007* (2013.01); *C03C 4/0021* (2013.01); *C03C 10/16* (2013.01)

(58) Field of Classification Search
CPC ......... A61K 33/42; A61K 33/08; A61K 8/25; A61K 33/16; A61K 6/0276; A61K 2300/00; A61K 33/00; A61K 6/033; A61K 6/0085; A61L 27/10; A61L 27/12; A61L 27/58
USPC .............................. 424/601, 52, 423, 724, 57
See application file for complete search history.

(56) References Cited

U.S. PATENT DOCUMENTS

| | | | |
|---|---|---|---|
| 4,643,982 A | 2/1987 | Kasuga | |
| 4,994,414 A * | 2/1991 | Yamamoto et al. | 501/12 |
| 5,318,929 A * | 6/1994 | Jana et al. | 501/10 |
| 5,634,956 A * | 6/1997 | Suh et al. | 65/33.1 |
| 6,244,871 B1 | 6/2001 | Litkowski | |
| 2007/0122356 A1 | 5/2007 | Kessler | |
| 2008/0226566 A1* | 9/2008 | Poth et al. | 424/52 |
| 2009/0208428 A1* | 8/2009 | Hill et al. | 424/52 |
| 2014/0056954 A1 | 2/2014 | O'Donnell et al. | |
| 2014/0193499 A1* | 7/2014 | Da Fonte Ferreira et al. | 424/489 |

FOREIGN PATENT DOCUMENTS

| | | |
|---|---|---|
| DE | 3306648 | 9/1983 |
| DE | 19812278 | 9/1999 |
| JP | 60239341 | 11/1985 |
| WO | 91/12212 | 8/1991 |
| WO | 2006/050829 | 5/2006 |

OTHER PUBLICATIONS

International Search Report for corresponding patent application No. PCT/GB2011/000958 dated Oct. 18, 2011.
Written Opinion for corresponding patent application No. PCT/GB2011/000958 dated Oct. 18, 2011.
Current Claims of U.S. Appl. No. 13/381,392, filed Aug. 17, 2013.

* cited by examiner

*Primary Examiner* — Frederick Krass
*Assistant Examiner* — Tracy Liu
(74) *Attorney, Agent, or Firm* — Renner, Otto, Boisselle, Sklar, LLP

(57) ABSTRACT

A bioactive glass composition comprising one or more glasses comprising $SiO_2$, $P_2O_5$ and a fluoride, the $SiO_2$ content being less than 40 mole %, the $P_2O_5$ content being at least 4 mole %, and the fluoride content being greater than 1 mole %. The bioactive glass or glass-ceramic can be used in a number of medical applications, including dental applications such as toothpaste.

18 Claims, 8 Drawing Sheets

BIOACTIVE GLASS COMPOSITION

This application is a national phase of International Application No. PCT/GB2011/000958 filed 24 Jun. 2011 and published in the English language.

The present invention relates to a bioactive glass composition.

A biologically active (or bioactive) material is one which, when implanted into living tissue, induces formation of an interfacial bond between the material and the surrounding tissue. Bioactive glasses are a group of surface-reactive glasses, which exhibit bioactivity. The bioactivity of these glasses is the result of complex reactions which take place on the surface of the glass under physiological conditions, and which result in the formation of hydroxycarbonated apatite (HCA) on the surface of the glass. The term "bioactive glass" as used herein is intended to encompass bioactive glass-ceramics as well as bioactive glasses. Bioactive glass-ceramics are similar to bioactive glasses but contain a crystalline phase in addition to the glass phase.

Because of the ability of bioactive glasses to bond with living tissue, and in particular bone, they are used in a number of medical applications, including dental applications such as toothpaste.

For many applications, and in particular for toothpastes, it is preferable that the glass phase should release fluoride and form fluorapatite (FAP), instead of HCA. This is because FAP is more resistant to acid dissolution in oral fluids than HCA and aids in the prevention of dental caries. Moreover, fluoride ions are known to aid apatite formation and stimulate the cell division of osteoblasts, the bone forming cells. For these reasons, fluoride may be incorporated into bioactive glasses.

While it is desirable to incorporate a fluoride in a bioactive glass, it has been found that, if the fluoride content of a glass is too high, it will result in the formation of fluorite ($CaF_2$) at the expense of fluorapatite when the glass is immersed in a body fluid.

Another problem that has been found with existing bioactive glasses is that they are very abrasive towards enamel and can result in excessive and undesirable wear of enamel. This is because the known glasses are harder than enamel. The common bioactive glass (45S5) used currently has a measured hardness of 4.58 GPa compared to enamel at approximately 3.5 GPa.

It is an object of the invention to seek to mitigate these problems which have been found with existing bioactive glasses.

The invention provides a bioactive glass composition comprising one or more glasses/glass-ceramics comprising $SiO_2$, $P_2O_5$ and a fluoride, the $SiO_2$ content being less than 40 mole %, the $P_2O_5$ content being at least 4 mole %, and the fluoride content being greater than 1 mole %.

The applicant has found that the tendency of FAP formation to be suppressed at higher concentrations of fluoride is reduced in glasses with a relatively low $SiO_2$ content and a relatively high phosphate content.

In addition, the applicants have found that glasses with a relatively low $SiO_2$ content and a relatively high phosphate and fluoride content have lower hardness values and so are softer and less abrasive towards enamel.

Moreover, the applicants have found that such glasses form apatite not only in simulated body fluid (SBF), but also readily in Tris buffer at pH 7.25.

The bioactivity of bioactive glasses is usually studied using an ISO Standard, ISO 23317. Under this standard, the glass is immersed in SBF, a saturated calcium and phosphate solution that mimics the ionic concentrations found in body fluids/ blood plasma. If the glass results in the formation of HCA within the time period designated under the standard, then it is termed bioactive. For the purposes of the present patent we extend this definition to include the formation of fluorapatite.

Although bioactivity is usually studied using ISO Standard, ISO 23317, this standard is not particularly suitable for studying bioactivity within the mouth. The reason for this is that saliva is somewhat diluted after taking in liquids and is often no longer saturated with regard to $Ca^{2+}$ and $PO_4^{3-}$. For this reason, bioactivity may also be investigated using Tris buffer, a simple buffer solution at pH=7.25 which contains no $Ca^{2+}$ and $PO_4^{3-}$. This represents a far more severe test of bioactivity.

Accordingly, the fact that compositions according to the invention have been shown to rapidly form FAP following immersion in Tris buffer has particular relevance for dental applications such as toothpastes.

Not only do the compositions according to the invention form apatite in Tris buffer, they also form more apatite than existing bioactive glasses and they form apatite faster than existing bioactive glasses. Thus, in tests, glasses with a low $SiO_2$ content and a high phosphate content have shown very rapid formation of FAP in under six hours, following immersion in Tris buffer at pH=7.25.

The $SiO_2$ content of the glass composition is preferably less than 39 mole %, more preferably less than 38 mole % most preferably less than 35 mole %. The $SiO_2$ content is preferably more than 25 mole %.

The $P_2O_5$ content is preferably greater than 4.5 mole %, more preferably greater than 5 mole %. The $P_2O_5$ content is preferably less than 10 mole %, more preferably less than 7 mole %.

The applicant has found that incorporating fluoride in the glass composition aids FAP formation, provided that an excessive amount of fluoride is not used. The applicant has also found that higher fluoride contents reduce hardness, which correlates with the glass transition temperature, Tg. The glass composition should therefore preferably have the highest possible fluoride content which is consistent with forming FAP and no fluorite.

Accordingly, the fluoride content is preferably greater than 3 mole %, more preferably greater than 4 mole %, most preferably greater than 5 mole %. The fluoride content is preferably less than 25 mole %, more preferably less than 18 mole %.

Strontium may be used to replace calcium and is known to enhance bioactivity. Strontium has a well documented anti caries function and mixed calcium/strontium apatites have a lower solubility product than either the equivalent calcium or strontium apatites. Accordingly, the composition preferably comprises up to 57 mole % of CaO and SrO combined, more preferably up to 50 mole % of CaO and SrO combined.

In high-phosphate containing glasses, the lower charge to size ratio of the $Sr^{2+}$ cation may result in the crystallisation of the glass, which is often undesirable as it reduces the solubility of the glass. Moreover sources of strontium are also much more expensive than sources of calcium which is important when the glasses are to be used in consumer health care products such as toothpaste. Accordingly, the composition preferably comprises less than 30 mole % SrO.

Potassium salts are often added to toothpaste formulations in order to treat dentine hypersensitivity and potassium may be used to replace sodium in the glass for this purpose. Accordingly, the composition may comprise up to 40 mole % $K_2O$.

It is important to note, however, that high K/Na ratios are potentially undesirable with regard to their effect on cells. For glasses used in medical applications such as bone substitutes and periodontal treatment a K/Na ratio close to that found in blood plasma of 0.04 is preferred.

Zinc may also be incorporated into the glass. Zinc inhibits apatite formation and is thought to block sites on the apatite crystal lattice and hinder apatite crystal growth. However zinc is often incorporated into toothpastes for its antibacterial and antigingivitis effects. Low zinc plasma levels which occur in many over sixty year olds are also often associated with poor wound healing rates and osteoporosis. Low zinc contents are attractive in glasses for both dental and medical applications for these reasons. Accordingly, the composition may comprise up to 5 mole % ZnO and $ZnF_2$ combined.

The composition may comprise up to 12 mole % of MgO and $MgF_2$ combined. Like zinc, magnesium acts to suppress apatite crystal growth.

One of the problems with bioactive glasses is that, whilst they dissolve rapidly and form amorphous phases rapidly, the crystallisation process to form an apatite is generally slow. Whilst fluoride speeds this process up, the applicant has found that adding an apatite further accelerates the process.

Accordingly, the composition may comprise an apatite. Preferably, the composition comprises at least 0.1 wt % of an apatite. The apatite may be hydroxycarbonated apatite or it may be hydroxyl apatite, but it is preferably fluorapatite. Preferably, the apatite is crystallised, and the size of the crystals is in the range 30 nm to 5 microns, preferably 30 nm to 3 microns.

The apatite crystals are thought to act as seed nuclei for the formation of apatite and apatite nucleation is thought to be the slow step in the crystallisation of apatite from solution, whilst crystal growth is thought to be rapid. Thus adding an apatite reduces the time to form new apatite from solution.

Small crystals are preferred for this process with a large surface area and a large number density. However small crystals are also desirable as they can enter the dentinal tubules (which are typically 3-5 microns in diameter) and allow more apatite to form on them sealing and blocking the dentinal tubules. This process is shown schematically in FIG. 1. A further advantage of using an apatite to seed the nucleation process is that larger bioactive glass particles may be used without the need to have a significant fraction of small (<5 microns) bioactive glass particles in the particle size distribution. Such small particles are prone to dissolution and surface reaction with trace amounts of water in the suspending media such as glycerol used for forming the toothpaste.

As an alternative to adding seed apatite crystals to the composition, the glass(es) of the invention may be pre-treated so that they have crystallised to fluorapatite on their surface. This fluorapatite may be a calcium fluorapatite or a mixed fluorapatite comprising strontium.

The surface fluorapatite may have a crystal size less than 5 microns, preferably less than 1 micron.

The pre-treatment may take the form of treatment with SBF or Tris buffer. Alternatively, in the case of fluorine-containing glasses with high phosphate content and low alkali metal content, the glasses may be heat treated at a temperature of between 400 and 850° C. to selectively crystallise fluorapatite on their surface.

The bioactive glass compositions of the invention may be used for various dental applications including promoting remineralisation of teeth, preventing caries, blocking dentinal tubules, treating dentine hypersensitivity and treating periodontal disease. They may also be used for various medical applications including use as a bone substitute.

A number of specific embodiments of the invention will now be described by way of example only with reference to the accompanying drawings of which:

FIG. 9b shows the quantitative determination of proportion of residual orthophosphate species in the glass and formation of FAp obtained by deconvolution of $^{31}P$ MAS-NMR spectra from FIG. 9a;

EXAMPLES

Figure 1:
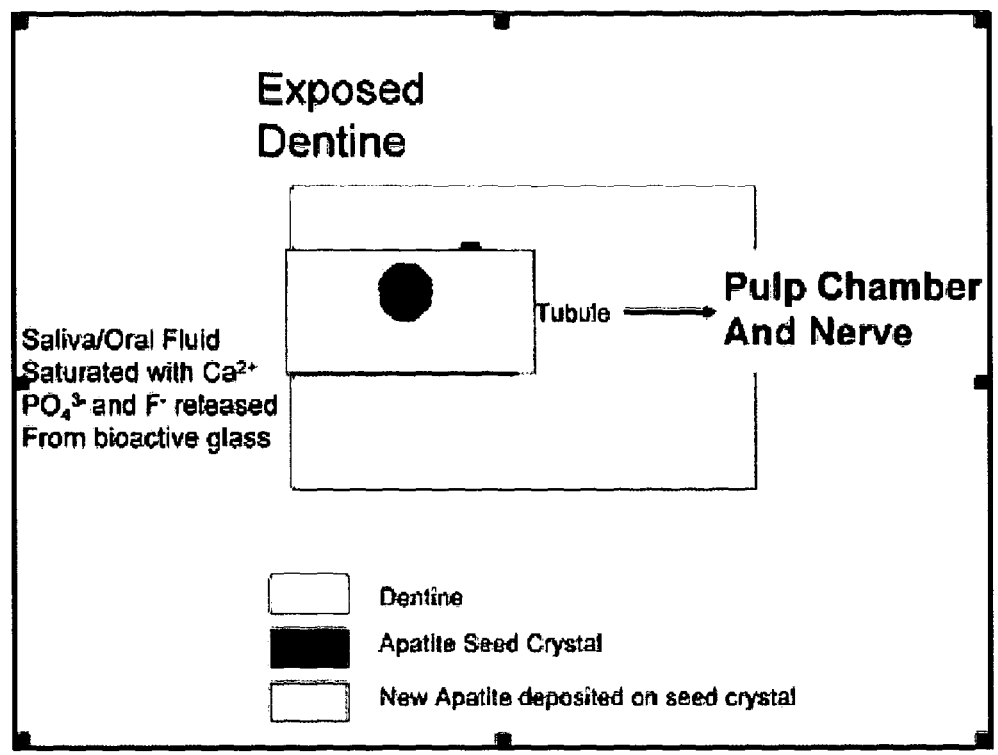
FIG. 1 shows schematically the blocking of dentinal tubules using a seed apatite crystal to nucleate further crystallisation of apatite from solution.
Figure 2:
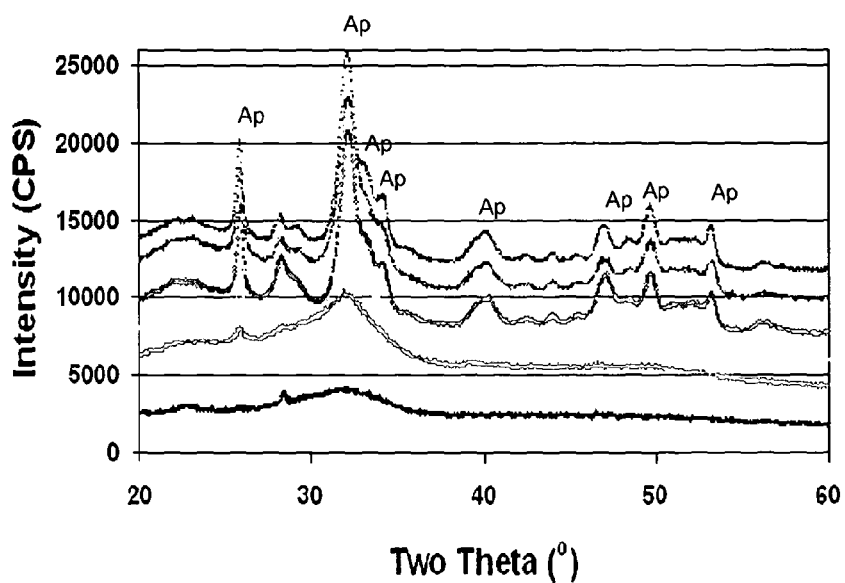
FIG. 2 shows XRD diffraction patterns of QMMM1 glass after immersion in Tris buffer in order bottom to top 3, 6, 9, 24, 72 and 168 Hrs. Ap=Fluorapatite.
Figure 3:
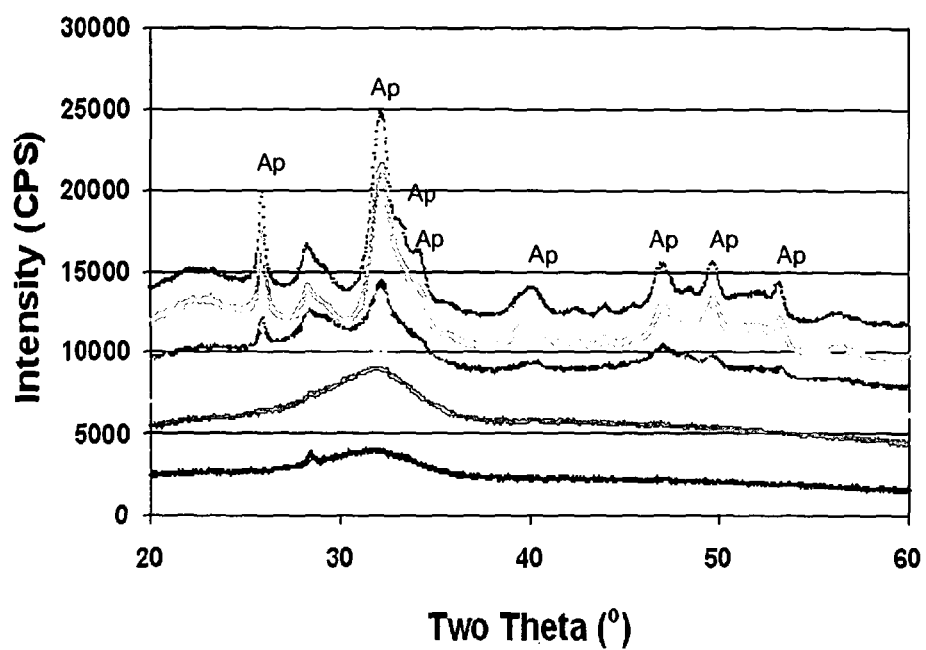
FIG. 3 shows XRD diffraction patterns of QMMM2 glass after immersion in Tris buffer in sequential order bottom to top 3, 6, 9, 24, 72 and 168 Hrs. Ap=Fluorapatite.

The glass compositions shown in Table 1a were synthesised by a melt quench route.

For each composition, appropriate amounts of the oxides and fluorides listed in Table 1a were weighed out to give approximately 200 g of batch. In the case of the oxides of calcium, strontium, sodium and potassium, the respective carbonates were used instead of the oxides. The batch was thoroughly mixed then placed in a 300 ml platinum/rhodium crucible. The temperature was raised to between 150 and 1550° C. and held at that temperature for 1.5 Hrs. The resulting melt was then shock quenched into water to produce a granular glass which was washed with ethanol and dried immediately at 125° C. for 1 hour. The glass was then ground in a vibratory puck mill and sieved to give a particle size less than 45 microns prior to characterisation.

TABLE 1a

Illustrative examples of glass compositions in mole percent

| Glass | Code | SiO$_2$ | P$_2$O$_5$ | Na2O | CaO | SrO | NaF | CaF$_2$ | SrF$_2$ | K$_2$O | ZnO |
|---|---|---|---|---|---|---|---|---|---|---|---|
| 1 | 45S5 | 46.1 | 2.6 | 24.3 | 26.9 | 0.0 | 0.0 | 0.0 | 0.0 | 0.0 | 0.0 |
| 2 | ICIE1 | 49.6 | 1.1 | 26.4 | 23.1 | 0.0 | 0.0 | 0.0 | 0.0 | 0.0 | 0.0 |
| 3 | QMMM1 | 34.8 | 5.8 | 22.7 | 28.0 | 0.0 | 8.7 | 0.0 | 0.0 | 0.0 | 0.0 |
| 4 | QMSMD | 35.5 | 5.9 | 27.6 | 24.1 | 0.0 | 0.0 | 6.9 | 0.0 | 0.0 | 0.0 |
| 5 | QMMM2 | 31.7 | 5.3 | 16.1 | 30.0 | 0.0 | 17.0 | 0.0 | 0.0 | 0.0 | 0.0 |
| 6 | QMMM3 | 29.0 | 4.8 | 10.5 | 31.7 | 0.0 | 24.0 | 0.0 | 0.0 | 0.0 | 0.0 |
| 7 | QMMM4 | 26.6 | 4.4 | 5.6 | 33.2 | 0.0 | 30.2 | 0.0 | 0.0 | 0.0 | 0.0 |
| 8 | QMMM5 | 28.4 | 4.7 | 22.1 | 19.3 | 0.0 | 0.0 | 25.5 | 0.0 | 0.0 | 0.0 |
| 9 | QMMM6 | 25.7 | 4.3 | 19.9 | 17.4 | 0.0 | 0.0 | 32.7 | 0.0 | 0.0 | 0.0 |
| 10 | QMMM7 | 34.6 | 5.7 | 0.0 | 50.4 | 0.0 | 0.0 | 9.3 | 0.0 | 0.0 | 0.0 |
| 11 | QMEL4 | 44.0 | 5.0 | 10.0 | 15.0 | 16.7 | 0.0 | 0.0 | 0.0 | 8.3 | 1.0 |
| 12 | QMEL5Na | 42.5 | 4.8 | 5.1 | 16.8 | 18.0 | 8.9 | 0.0 | 0.0 | 8.0 | 1.0 |
| 13 | QMEL6 | 40.2 | 4.6 | 9.1 | 13.7 | 15.2 | 0.0 | 4.7 | 4.0 | 7.6 | 0.9 |
| 14 | QMEL7 | 38.4 | 4.4 | 8.7 | 13.1 | 14.5 | 0.0 | 6.9 | 5.9 | 7.2 | 0.9 |
| 15 | QMEL8 | 36.7 | 4.2 | 8.3 | 12.5 | 13.9 | 0.0 | 9.0 | 7.7 | 6.9 | 0.8 |
| 16 | QMEL9 | 33.4 | 3.8 | 7.6 | 11.4 | 12.6 | 0.0 | 13.0 | 11.1 | 6.3 | 0.8 |
| 17 | QMEL10 | 30.3 | 3.4 | 6.9 | 10.3 | 11.5 | 0.0 | 16.7 | 14.4 | 5.7 | 0.7 |
| 18 | QMIF2 | 35.9 | 5.9 | 4.9 | 48.9 | 0.0 | 5.8 | 0.0 | 0.0 | 0.0 | 0.0 |
| 19 | QMIF3 | 35.9 | 5.9 | 7.3 | 46.4 | 0.0 | 5.8 | 0.0 | 0.0 | 0.0 | 0.0 |
| 20 | QMIF4 | 35.9 | 5.9 | 9.7 | 43.9 | 0.0 | 5.8 | 0.0 | 0.0 | 0.0 | 0.0 |
| 21 | CaNaR1 | 34.5 | 6.3 | 14.5 | 38.9 | 0.0 | 5.8 | 0.0 | 0.0 | 0.0 | 0.0 |
| 22 | CaNaR2 | 34.5 | 6.3 | 19.3 | 34.1 | 0.0 | 5.8 | 0.0 | 0.0 | 0.0 | 0.0 |
| 23 | CaNaR3 | 34.5 | 6.3 | 24.2 | 29.2 | 0.0 | 5.8 | 0.0 | 0.0 | 0.0 | 0.0 |
| 24 | CaNaR4 | 34.5 | 6.3 | 29.0 | 24.4 | 0.0 | 5.8 | 0.0 | 0.0 | 0.0 | 0.0 |
| 25 | PhoIn4 | 35.6 | 5.8 | 25.2 | 27.6 | 0.0 | 5.8 | 0.0 | 0.0 | 0.0 | 0.0 |
| 26 | PhoIn5 | 31.7 | 7.7 | 26.1 | 28.7 | 0.0 | 5.8 | 0.0 | 0.0 | 0.0 | 0.0 |

Note
Glasses 1-2 and 11 are included for comparison purposes only and are not according to the invention.

Table 1a includes a number of glasses not covered by the present invention for comparison purposes, including the well known 45S5 glass composition (Glass 1) and the extensively studied and characterised ICIE1 glass composition (Glass 2). These compositions are typical of those used commercially. Also included for comparison is Glass 11, which includes no fluoride, and Glasses 12, 13, 16 and 17 which include various fluoride contents.

In the existing patents and the majority of the published scientific literature, bioactive glasses are generally expressed in weight percent. However since SiO$_2$, CaO and Na$_2$O have similar molecular weights (60, 56 and 62 respectively), an amount given in weight percent does not significantly alter when converted to mole percent.

Glasses 3 and 5-8 have SiO$_2$ contents below 35 mole % and would be regarded as highly invert glasses. An invert glass is a glass where there is less than 50 mole percent of the SiO$_2$ the network forming oxide. Highly invert glasses are highly disrupted and are prone to crystallisation and are generally difficult to form. However they are very surface reactive and dissolve readily which is a very desirable feature for a bioactive glass. Glasses 6 to 8 have SiO$_2$ contents below 30 mole %. It is generally considered impossible to produce highly invert glasses (ie with <40 mole % SiO$_2$) without resorting to very specialised rapid quenching methods. It was therefore surprising to be able to synthesise glasses with silica contents well below 40 mole % with conventional quenching.

Glass composition 9 (QMMM6) has an exceptionally high fluoride content, and exploded on contact with water during fritting, that is, on pouring the molten liquid glass rapidly into water to produce a granular glass. It is thought that this glass reacted vigorously with water.

TABLE 1b

Compositions of sodium free glasses

| | SiO$_2$ | CaO | P$_2$O$_5$ | CaF$_2$ | Ca:P | F:P | T$_m$ (° C.) | As Quenched Glass |
|---|---|---|---|---|---|---|---|---|
| QMXJC14 | 38.1 | 55.5 | 6.3 | 0 | 4.4 | 0.0 | 1550 | Amorphous |
| QMXJC01 | 37.0 | 53.9 | 6.1 | 3.0 | 4.6 | 0.5 | 1550 | Amorphous |
| QMXJC02 | 36.4 | 53.0 | 6.0 | 4.5 | 4.8 | 0.8 | 1500 | Amorphous |
| QMXJC03 | 35.9 | 52.2 | 6.0 | 6.0 | 4.9 | 1.0 | 1500 | Amorphous |
| QMMM7 | 34.6 | 50.4 | 5.7 | 9.3 | 5.2 | 1.6 | 1450 | FAp |
| QMXJC04 | 32.9 | 48.0 | 5.5 | 13.6 | 5.6 | 2.5 | 1450 | FAp + C |
| QMXJC05 | 31.4 | 45.7 | 5.2 | 17.8 | 6.1 | 3.4 | 1450 | FAp + C + CaF$_2$ |
| QMXJC06 | 28.4 | 41.4 | 4.7 | 25.5 | 7.1 | 5.4 | 1450 | FAp + C + CaF$_2$ |

High fluorite content glasses from Table 1b crystallised to fluorine containing crystal phases such as FAP cuspidine (Ca$_4$Si$_2$O$_9$F$_2$) and fluorite upon quenching. The amorphous glasses in Table 1 all formed large amounts of apatite within 24 hours in both Tris buffer and SBF. The high melt temperatures of the low fluoride content glasses is undesirable for economic reasons Each of the glasses of Table 1a was immersed in a Tris Buffer solution at a concentration of 75 mg in 50 ml. The Tris Buffer was prepared as follows:

7.545 g of Tris(hydroxymethyl)amino methane (THAM) was transferred into a graduated flask filled with approximately 400 ml of deionised water. Once the THAM had dissolved, 22.1 ml of 2N HCl was added to the flask, which was then made up to 1000 ml with deionised water and adjusted to pH 7.25 at 37° C.

All of the Glasses in accordance with the invention formed apatite when immersed in the Tris buffer. Comparative Glasses 1-2 and 11 did not form significant quantities of apatite when immersed in the Tris buffer. As discussed above, immersion in Tris buffer represents a far more severe test of bioactivity than the standard test for bioactivity which determines whether the glass forms an apatite in SBF.

FIGS. 2 to 11 illustrate the invention.

75 mg of glasses 11 to 16 with a particle size <45 microns were added to 50 ml of Tris buffer at pH 7.25 along with a 1 mm slice cut through the mid coronal section of a human tooth section treated with 10% citric acid to expose the dentinal tubules.

After periods of 3, 6, 9, 24, 72 and 168 Hrs the tooth section was recovered and the solution filtered. The resulting solid was dried at 37° C. and examined by Fourier Transform Infrared spectroscopy (FTIR), X-ray powder diffraction (XRD) and solid state Magic Angle Spinning—Nuclear Magnetic Resonance (MAS-NMR) spectroscopy looking at $^{19}$F and $^{31}$P. The pH of the solution was measured and the free fluoride ion concentration was also measured.

X-ray powder diffraction and FTIR spectroscopy showed the presence of a crystalline apatite formed in solution from 6 Hrs with a split phosphate band at approximately 560 cm$^{-1}$ and 600 cm$^{-1}$. The amount of apatite formed increased in time up to 24 Hrs. $^{19}$F and $^{31}$P MAS-NMR showed the apatite to be a fluorapatite with a characteristic peak with a chemical shift at −103 ppm in the $^{19}$F MAS-NMR spectra and a peak at 2.9 ppm in the $^{31}$PMAS-NMR spectra corresponding to fluorapatite.

Figure 7:
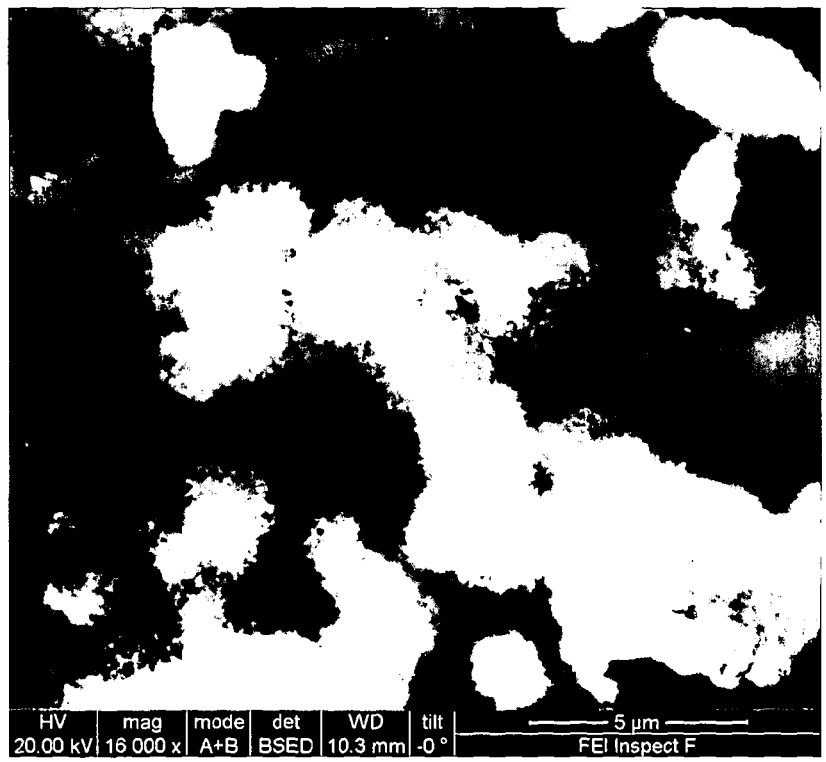
FIG. 7 shows a typical example of blocked dentinal tubules by fluorapatite crystals following etching with citric acid and after exposure to glass QMEL7 for 168 Hrs in Tris buffer.

Examination of the dentine slices by scanning electron microscopy showed the dentinal tubules to be open prior to treatment with the bioactive glasses (FIG. 6) and to be occluded after treatment with a calcium phosphate ratio close to that of apatite at 1.6 (FIG. 7).

The same procedure was repeated for Glass 1 which is the well known 45S5 glass. XRD and FTIR showed that no significant apatite had been formed under these conditions and there was no occlusion of the dentinal tubules under these conditions.

FIGS. 2-5 show the formation of apatite after immersion of the glasses in Tris buffer for various times.

Figure 4:
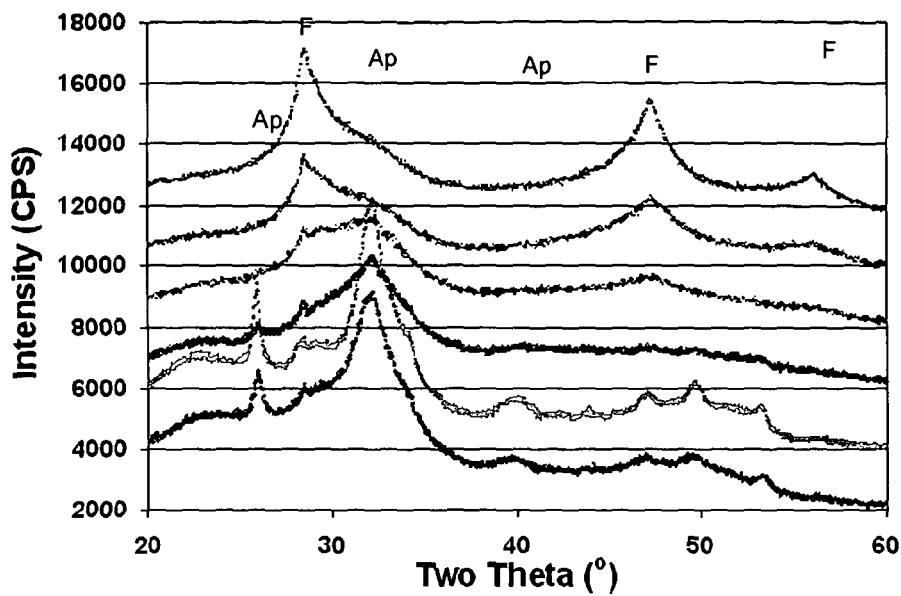
FIG. 4 shows XRD of Glasses 3 to 8 after 9 Hrs in Tris buffer in order of increasing fluorine content. Ap=Fluorapatite, F=Fluorite.

FIG. 4 shows the formation of apatite and fluorite in Glasses 3 to 8 after 9 hours immersion in Tris buffer. The formation of fluorite at the expense of fluorapatite is seen at higher fluoride contents in the glass.

Figure 5:
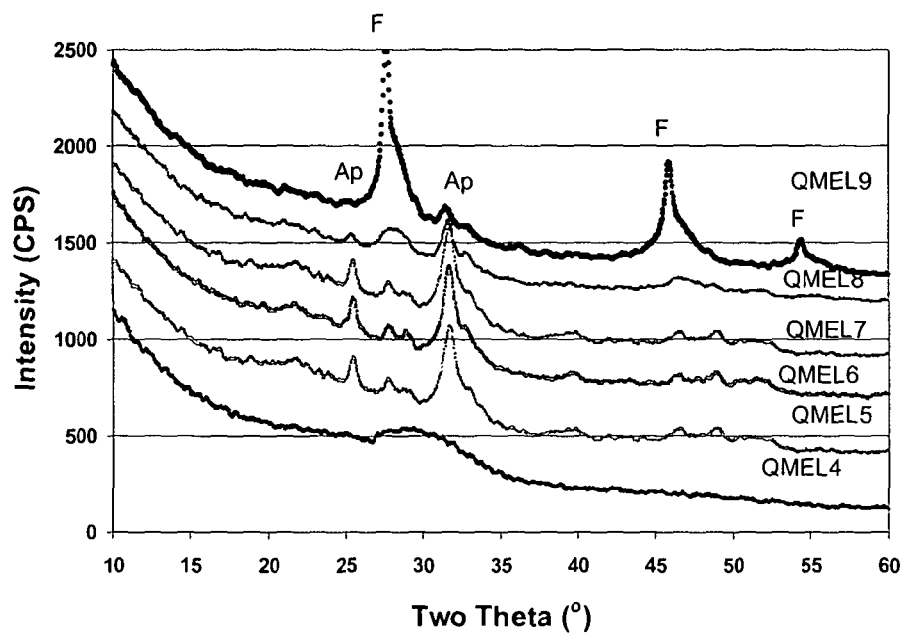
FIG. 5 shows XRD patterns of Glasses 11 to 16 after 168 Hrs in Tris buffer. Note the absence of sharp diffraction lines corresponding to apatite in the fluorine free glass QMEL4 and the presence of fluorite in the high fluorine content glasses.
Figure 6:
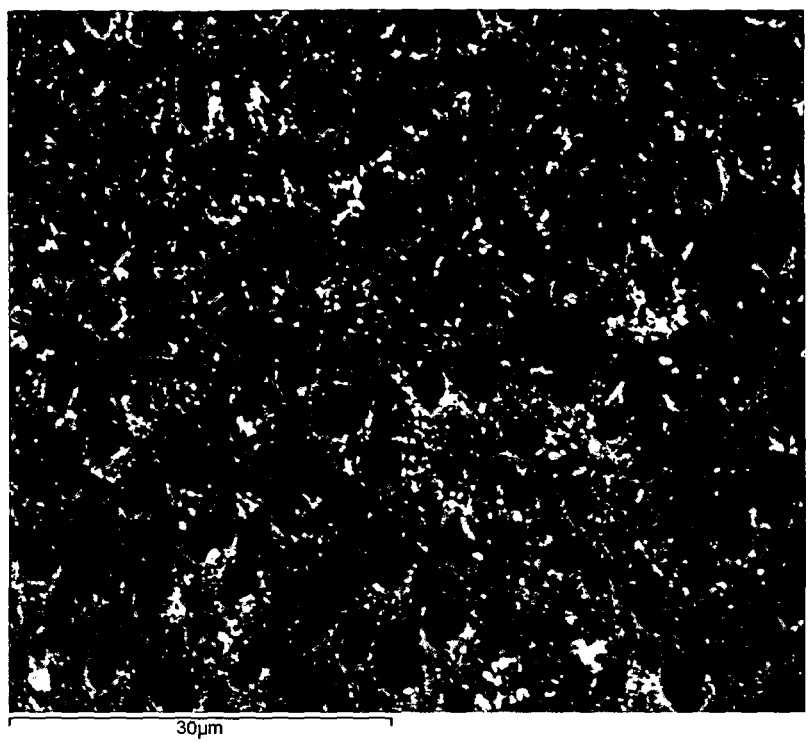
FIG. 6 shows open dentinal tubules in human dentine after exposure to 10% citric.

FIG. 5 shows the XRD diffraction patterns obtained for multicomponent Glasses 11-16 containing Sr, Zn and K after immersion in Tris buffer for 168 hours. The fluoride free glass, Glass 11, forms no apatite whilst the glasses containing fluoride form apatite until the glass contains 18 mol % MF$_2$ where M is Ca and Sr, after which both fluorapatite and fluorite form. Above 18 mol % MF$_2$, the glass forms predominantly fluorite and relatively little fluorapatite. It can be seen clearly that incorporating fluoride in the glass composition aids fluorapatite formation providing excessive amounts of fluoride are not used. There therefore exists an optimum fluoride content for FAp formation.

Figure 8:
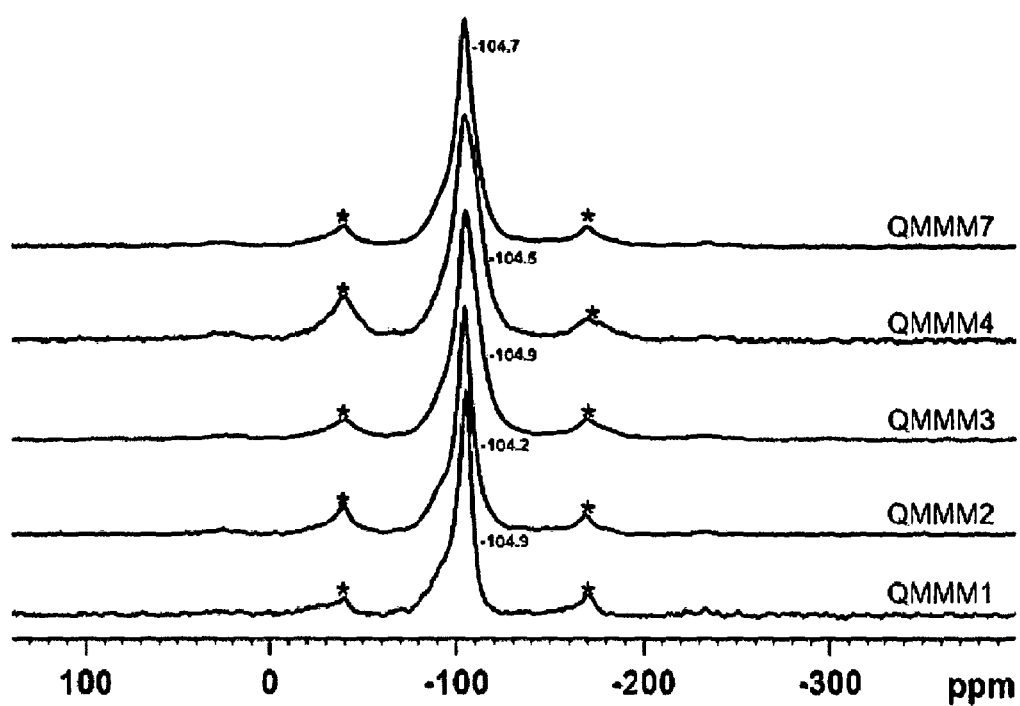
FIG. 8 shows $^{19}F$ MAS-NMR spectra of high phosphate fluorine containing glasses after immersion in Tris buffer after 3 days.
Figure 9A:
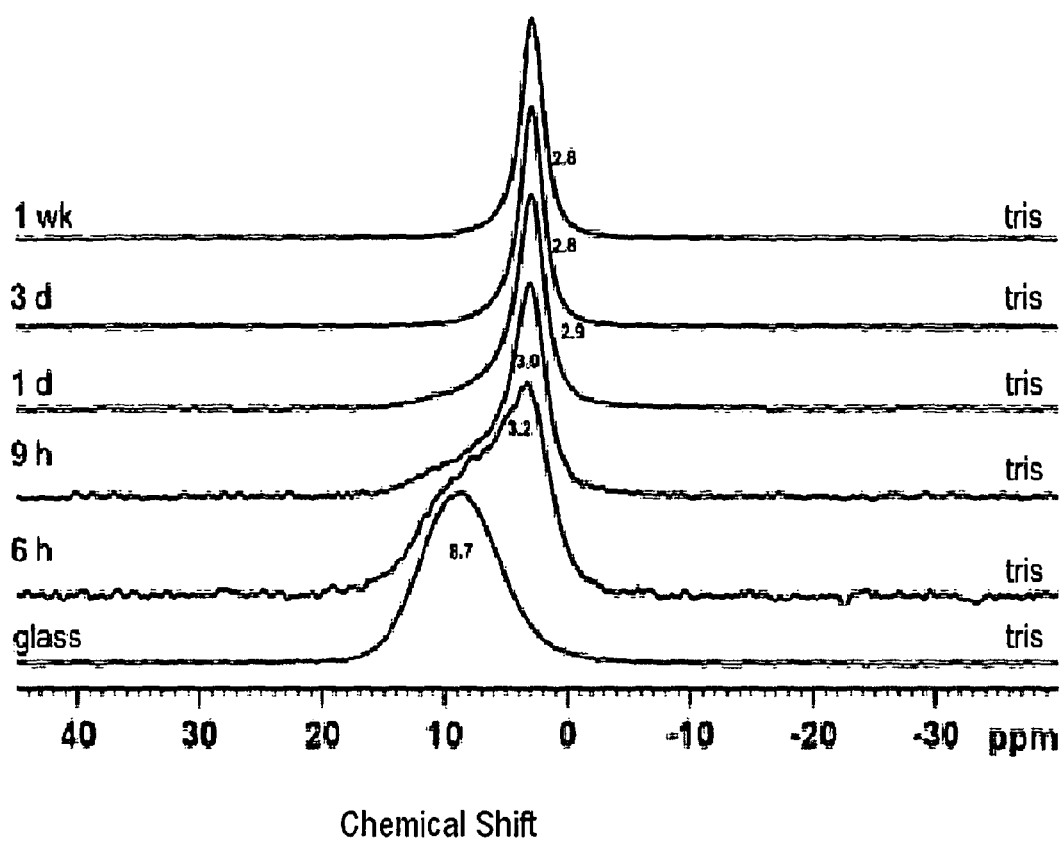
FIG. 9a shows $^{31}P$ MAS-NMR spectra for QMMM1 as a function of immersion time in Tris buffer.
Figure 9B:
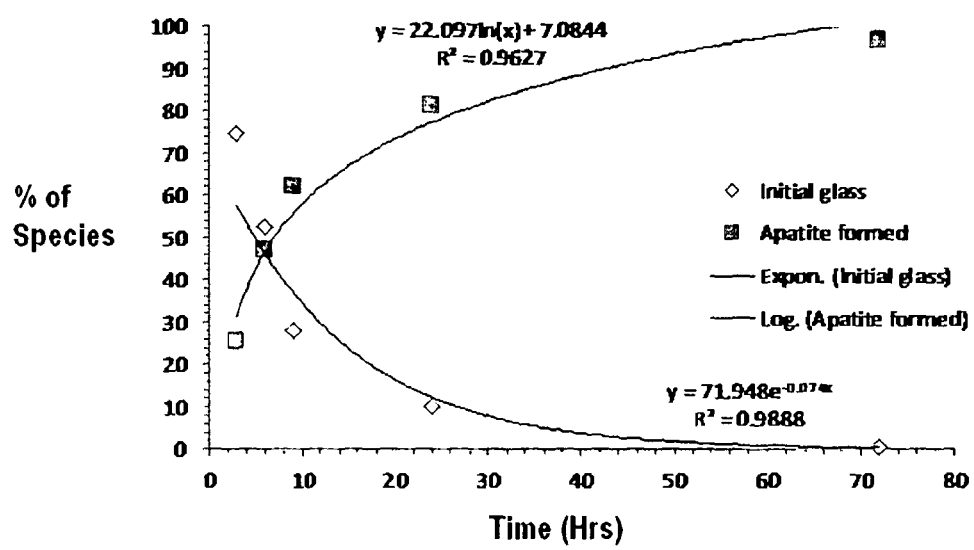

FIG. 8 shows $^{19}$F MAS-NMR spectra for glasses after immersion in Tris buffer showing the characteristic peak for Fap at −103 ppm. FIG. 9a shows $^{31}$P MAS-NMR spectra for Glass 4 (QMMM1) following immersion in Tris buffer at pH=7.25 for time periods from 0 to 168 Hrs. The phosphorus is present in the initial glass as a mixed Ca/Na orthophosphate species with a chemical shift of approximately 9 ppm. Following the immersion the original peak disappears and is progressively replaced by a new peak at about 3 ppm corresponding to a calcium orthophosphate of which FAP is an example. Deconvolution of the spectra enables quantification of the proportions of glass and FAP as a function of time which are shown in FIG. 9b. It can be seen that this glass forms FAP very rapidly and FAP forms in under 6 Hrs.

Figure 10:
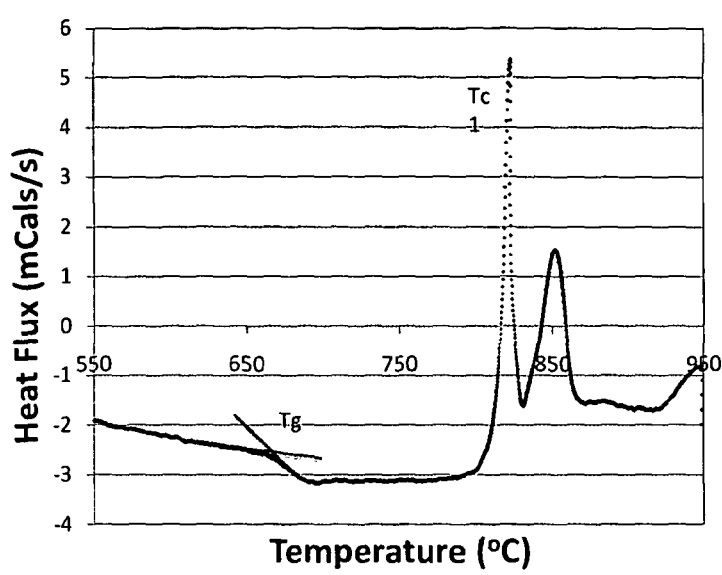
FIG. 10 shows a differential scanning calorimetry trace of Glass QMIF3 showing the glass transition temperature and crystallization exotherms.

FIG. 10 shows the DSC trace for glass 18 QMIF3 Table 1a This glass has a low sodium content and a Tg of about 670° C. The first crystallisation exotherm, Tc1 corresponds to the crystallisation of FAP. Heat treating this glass to 800° C. results in the formation of FAP, which acts as seed crystals for further FAP formation and accelerates the formation of further FAP when immersed in Simulated Body Fluid or Tris buffer. This FAP glass-ceramic may be used either as an additive for toothpastes or as a bone substitute. This glass with its sodium content reduces the melt temperature to below 1500° C. which facilitates economical melting compared to glasses containing no alkali metal, as well as casting to form complex shapes required for custom made bone protheses. The higher calcium content compared to glasses of the QMMM1 to QMMM5 series facilitates the formation of FAP in Tris buffer and SBF.

FAP was synthesised by mixing tricalcium phosphate (Ca$_3$(PO$_4$)$_2$) and CaF$_2$ in powder form with a particle size <50 microns in the stoichiometric ratio for FAP. This mixture was then solid state reacted for 16 Hrs at 1050° C. in an alumina crucible. The resulting solid was ground and sieved to give a powder <5 microns. An XRD pattern of the powder showed it to be FAP The FAP was then added at a concentration of 2.5% to bioactive glass 4 QMSMD Following immersion of the glass/FAP mixture in Tris buffer it was found to accelerate apatite formation and resulting in larger FAP crystals as evidenced by reduced line broadening by XRD.

TABLE 2

Glass transition temperatures and calculated hardness values for example glasses.

| Glass | Code | Tg (° C.) | Hardness GPa) | NC |
|---|---|---|---|---|
| 1 | 45S5 | 530 | 4.98 | 2.11 |
| 2 | ICIE1 | 513 | 4.84 | 2.09 |
| 3 | QMMM1 | 484 | 4.60 | 2.08 |
| 4 | QMSMD | 450 | 4.32 | 2.08 |
| 5 | QMMM2 | 440 | 4.23 | 2.08 |
| 6 | QMMM3 | 416 | 4.03 | 2.08 |
| 7 | QMMM4 | 408 | 3.97 | 2.08 |
| 8 | QMMM5 | 383 | 3.76 | 2.08 |
| 9 | QMMM6 | — | — | 2.08 |
| 10 | QMMM7 | 663 | 6.08 | 2.08 |
| 11 | QMEL4 | 500 | 4.73 | 2.44 |
| 12 | QMEL5 | 480 | 4.57 | 2.43 |
| 13 | QMEL6 | 469 | 4.47 | 2.44 |
| 14 | QMEL7 | 454 | 4.35 | 2.44 |
| 15 | QMEL8 | 441 | 4.24 | 2.44 |
| 16 | QMEL9 | 425 | 4.11 | 2.44 |
| 17 | QMEL10 | 400 | 3.90 | 2.44 |
| 18 | QMIF2 | 700 | 6.39 | 2.08 |
| 19 | QMIF3 | 674 | 6.18 | 2.08 |
| 20 | QMIF4 | 630 | 5.81 | 2.08 |
| 21 | CaNaR1 | 575 | 5.35 | 2 |
| 22 | CaNaR2 | 523 | 4.92 | 2 |
| 23 | CaNaR3 | 487 | 4.62 | 2 |
| 24 | CaNaR4 | 462 | 4.42 | 2 |
| 25 | PhoIn1 | 485 | 4.61 | 2 |
| 26 | PhoIn4 | 487 | 4.62 | 2 |
| 27 | PhoIn5 | 483 | 4.59 | 2 |
| Enamel | | | 3.5 | |

Hardness calculated using an experimentally determined model where Hardness=0.0083*Tg+0.5812. Experimentally the hardness of the 45S5 glass was determined to be 4.68 GPa. close to the calculated value at 4.98 GPa. Note the hardness decreases with increasing fluorine content in the glass for glasses ICSW9 to QMMM5 and from QMEL4 to QMEL10.

Reduced hardness of the glass is an important factor with regard to abrasive wear of toothpastes and the bioactive glass should be no harder than that of enamel in order to avoid enamel wear during tooth brushing.

Figure 11:
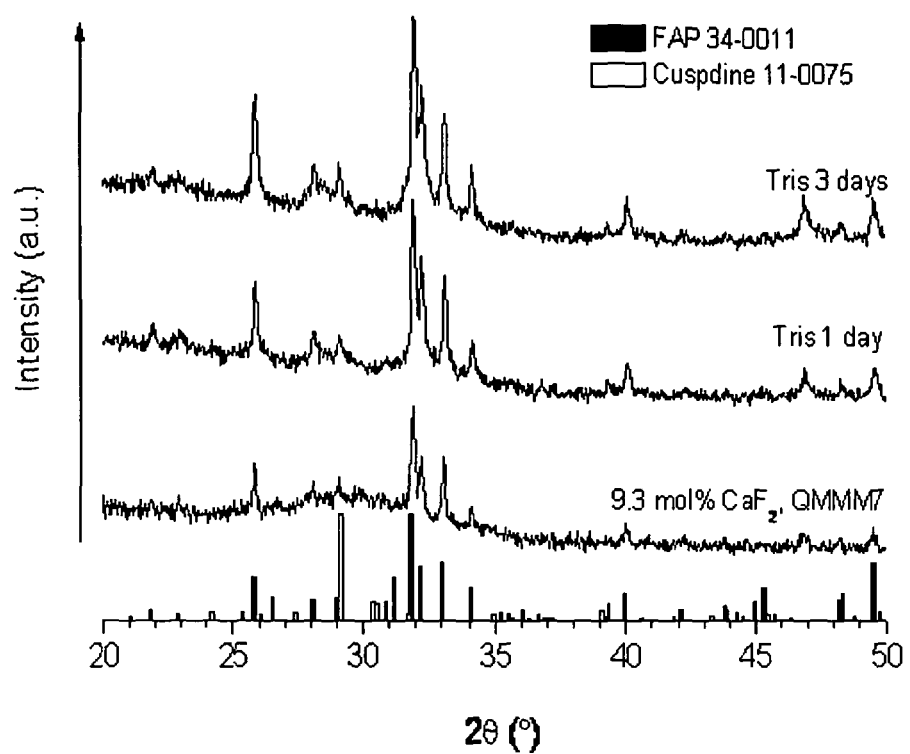
FIG. 11 shows the QMMM7 glass-ceramic.

FIG. 11 shows the QMMM7 glass-ceramic. The initial glass was found to contain FAp on slow quenching (Bottom Pattern) and is in fact a FAp glass-ceramic. On immersion of this glass in Tris buffer the amorphous glass phase dissolves forming more FAp. The FAp is thought to form on the existing FAp crystallites. The diffraction lines are much sharper indicating the FAp crystals are >50 nm in contrast to totally amorphous glasses in the absence of FAp Crystallites that give rise to broad diffraction lines corresponding to Nano sized FAp crystals (ie <50 nm). Similar results were obtained in SBF. Rapid quenching resulted in this glass being amorphous but crystallization of FAp could be achieved by heat treating at 783° C.

The above embodiments have been described to illustrate the invention, and are not intended to be limiting. The skilled person will be readily able to devise alternative embodiments without departing from the scope of the claims.

The invention claimed is:

1. A bioactive glass composition comprising one or more glasses comprising $SiO_2$, $P_2O_5$ and a fluoride, the $SiO_2$ content being less than 40 mole %, the $P_2O_5$ content being at least 4 mole %, and the fluoride content being greater than 1 mole % and less than 25 mole %, wherein the bioactive glass composition forms fluorapatite instead of hydroxycarbonated apatite (HCA) and suppresses formation of fluorite ($CaF_2$) at the expense of fluorapatite when immersed in a body fluid or in simulated body fluid.

2. The bioactive glass composition of claim 1, wherein the $SiO_2$ content is less than 39 mole %.

3. The bioactive glass composition of claim 1, wherein the $SiO_2$ content is more than 25 mole %.

4. The bioactive glass composition of claim 1, wherein the $P_2O_5$ content is greater than 4.5 mole %.

5. The bioactive glass composition of claim 1, wherein the $P_2O_5$ content is less than 10 mole %.

6. The bioactive glass composition of claim 1, wherein the fluoride content is greater than 3 mole %.

7. The bioactive glass composition of claim 1, wherein the composition comprises up to 57 mole % of CaO and SrO combined.

8. The bioactive glass composition of claim 1, wherein the composition comprises up to 40 mole % $K_2O$.

9. The bioactive glass composition of claim 1, wherein the composition comprises up to 5 mole % ZnO and $ZnF_2$ combined.

10. The bioactive glass composition of claim 1, wherein the composition comprises up to 12 mole % of MgO and $MgF_2$ combined.

11. The bioactive glass composition of claim 1, wherein the composition further comprises an apatite prior to immersion in the body fluid or in the simulated body fluid.

12. The bioactive glass composition of claim 11, wherein the composition comprises at least 0.1 weight percent of the apatite present prior to immersion in the body fluid or in the simulated body fluid.

13. The bioactive glass composition of claim 11 wherein the apatite present prior to immersion in the body fluid or in the simulated body fluid is fluorapatite.

14. The bioactive glass composition of claim 11 wherein the apatite present prior to immersion in the body fluid or in the simulated body fluid is crystallised from the glass, and the size of the crystals is in the range 30 nm to 5µ.

15. The bioactive glass composition of claim 1 wherein the glass(es) have been pre-treated so that they have crystallised fluorapatite on their surface prior to immersion in the body fluid or in the simulated body fluid.

16. The bioactive glass composition of claim 15, wherein the surface fluorapatite has a crystal size less than 5 µm.

17. The bioactive glass composition of claim 1, for use in dental applications or as a bone substitute.

18. A toothpaste comprising a bioactive glass composition according to claim 1.

* * * * *